United States Patent [19]
Andersson et al.

[11] Patent Number: 6,005,917
[45] Date of Patent: Dec. 21, 1999

[54] VELOCITY ADAPTIVE FILTERED ANGIOGRAPHY

[76] Inventors: Mats Andersson, Skedagatan 1A, S-582 37 Linköping; Hans Knutsson, Egnahemsgatan 11, S-582 47 Linköping; Torbjörn Kronander, Backhemmet lilla Tobo, S-590 50 Vikingstad, all of Sweden

[21] Appl. No.: 08/939,740

[22] Filed: Oct. 6, 1997

[30] Foreign Application Priority Data

Apr. 5, 1995 [SE] Sweden .................................. 950126

[51] Int. Cl.$^6$ .............................. H05G 1/64; A61B 6/00
[52] U.S. Cl. ...................................... 378/98.12; 382/130
[58] Field of Search .................................. 378/62, 98.12; 382/130

[56] References Cited

U.S. PATENT DOCUMENTS

| | | | |
|---|---|---|---|
| 4,677,478 | 6/1987 | Kruger et al. | 378/98.12 |
| 4,913,154 | 4/1990 | Ermert et al. | 600/431 |
| 5,053,876 | 10/1991 | Blissett et al. | 348/208 |
| 5,091,925 | 2/1992 | Haendle et al. | 378/98.2 |

FOREIGN PATENT DOCUMENTS

| | | |
|---|---|---|
| 0578311 | 1/1994 | European Pat. Off. . |
| 2257544 | 1/1993 | United Kingdom . |
| WO93/15658 | 8/1993 | WIPO . |

OTHER PUBLICATIONS

Bursch, "Functional Angiocardiography", Z. Kardiol. 78; Suppl. 7, 1989, pp. 181–186.

"Representing Local Structures Using Tensors", Hans Knutsson In the 6th Scandinavian Conf. on Image Analysis, pp. 244–251. Oulu, Finland, Jun. 1989. Computer Vision Lab, Linkoping Univ. Sweden '89.

"Robust N–Dimensional Orientation Estimation using Quadrature Filters and Tensor Whitening." In Proceedings of IEEE Int't. Conf. on Acoustics, Speech, & Signal Processing, Adelaide, Australia, Apr. 1994, IEEE, LiTH–I–SY–R–1798, H. Knutsson & M. Andersson.

"Controllable Multidimensional Filters in Low Level Computer Vision." PhD thesis, Linkoping University, Sweden, S–581 83 Linkoping, Sweden, Sep. 1992, Dissertation No. 282, ISBN 91–7870–981–4, M. Andersson.

"The Fornier Transform and its Applications." McGraw–Hill, 2nd Edition, 1986. R. Bracewell.

D.E. Dudgeon and R.M. Mersereau, Multidimensional Digital Signal Processing. Prentice–Hall signal processing series. Prentice–Hall 1984. ISBN 0–13–604959–1.

D.J. Fleet. Measurement of image velocity. Kluwer Academic Publishers, 1992. ISBN 0–7923–9198–5.

G.H. Grandlund and H. Knutsson. SIgnal Processing for Computer Vision. Kluwer Academic Publishers, 1995. ISBN 0–7923–9530–1.

*Primary Examiner*—David P. Porta
*Assistant Examiner*—David Vernon Bruce
*Attorney, Agent, or Firm*—Hayes Soloway Hennessey Grossman & Hage PC

[57] ABSTRACT

A method of imaging a blood vessel in a body using X-rays and an injectable contrast medium is described. The contrast medium is injected into the body, and signals constituted by an X-ray image sequence depicting X-ray attenuation values is recorded. The X-ray attenuated values in each spaced-time neighborhood are combined in a way that is dependent on the processed image sequence and separately established for each neighborhood, and separating, from background and vessel signals, flow signals having energy contributions mainly in an area of frequency domain bounded by surfaces corresponding to threshold velocities separately established for each neighborhood, which surfaces are shifted a specified amount along a temporal frequency axis.

43 Claims, 8 Drawing Sheets

VELOCITY ADAPTIVE FILTERED ANGIOGRAPHY

BACKGROUND OF THE INVENTION

In clinical examinations of blood vessels using X-ray technique (angiography) a contrast media is injected into the selected blood vessel to increase the contrast and the resolution of the blood vessels relative to the surrounding tissue. It is well known that a further increase of the image quality is achieved by un-mashing the contributions in the resulting image that is unaffected by the the contrast media e.g. bones. This method is commonly referred to as 'Digital Subtraction Angiography (DSA)' and require a series (or sequence) of at least two images recorded during the contrast injection. In the first image no contrast media is present (pre contrast) while in the following images the blood vessels which are injected by contrast media will appear with increased visibility while bone and tissue not being affected by the contrast media will give a constant contribution throughout the sequence. If two consecutive images from such an angiography sequence are subtracted, this operation will in an ideal case remove the static structures while rendering the blood vessels which are subject to contrast media without masking effects from surrounding body parts. Digital subtraction angiography is a well known and frequently used method which exists in a number of varieties. One of the most frequently used algorithms computes the absolute value of the difference between every consecutive image pair in the sequence. The result is then computed by seeking the maximal value for each individual image element (pixel) in the subtracted sequence. Successful use of subtraction angiography is dependent on the fact that all changes or rather motions, that occur in the image sequence are induced by the injection of the contrast medium. All external motions not induced by the contrast medium injection generate what is termed 'motion artifacts' when using traditional subtraction angiography algorithms. Disturbing artifacts will occur in the following cases 1. Noise Noise is present in the X-ray equipment and in the recording process where the registered intensity is digitized (quanfization noise).
2. Pure translation The patient fails to be immobile and translates the part of the body which is subject for the investigation during the recording.
3. Body motion The patient fails to be immobile and rotation is involved in the motion of the part of the body which is subject for the investigation during the recording.
4. Internal motion Motion of inner organs such as e.g. intestinal motions, movements of the lungs and the chest during breathing and the movements generated by the beating heart.

A rather small motion artifact is able to cause a substantial degradation in image quality. To avoid the costs as well as the risks and the suffering involved in a new recording it is of major importance that the effects of motion artifacts are reduced in the post processing of the angiography sequence. In case 2 above it is quite simple to restore the recording since the motion is uniform for all pixels belonging to the same image in the sequence. The sequence can consequently be restored by performing an equally large shift in the 'opposite direction' in the post processing for the images that where affected by the motion. This method is termed 'pixel shift'. Pixel shift is widely used and works satisfactory for such simple motion artifacts. The magnitude of the shift, however, needs to be defined by an human operator. The implementation of the pixel shift with sub-pixel accuracy is straight forward using fundamental signal processing methods [Bracewell, chapter 10].

Since the description of the new invention will be made in terms of spatio-temporal filters it may at this point be illuminating to express the above standard methods in filter terms to clarify the differences. The fundamental operation using DSA is to subtract two images. The recorded image sequence can be interpreted as a three dimensional space time signal with two spatial and one temporal dimension. In filter terminology a spatio-temporal filter performing subtraction consists of only two coefficients, plus and minus one, positioned on the temporal axis. The pixel shift operation, on the other hand, is performed separately for each single image in the sequence and the corresponding spatio-temporal filter has no temporal extent. To reduce artifacts induced by noise (case one above) it is known that a temporal filter tuned to the spectral content of the contrast injection envelope can be used, (U.S. Pat. No. 5,504,980). By this approach only the fractional part of the noise that 'varies' in the same pace as the contrast pulse will contribute to artifacts. A conventional DSA algorithm is applied after this preprocessing step. Common for the above operations is that the shape of these filters are global, i.e. constant for a whole image or for the entire sequence. Using established methods there is consequently no possibility to adapt the filters to motions that only occur locally in a small environment of the spatio-temporal signal e.g. the type of motions that are described in point three and four above. Consider for example a recording of a heart where the coronary arteries are subject to the motions of the heart beats as well as the motions induced by the contrast medium.

The velocity and direction of the movements of the heart vary locally over the image and over time. There is no possibility that the above described methods could be expected to restore such complex angiography sequences with satisfactory result. The support for this invention rests on the advanced image processing tools which have been developed for local image sequence structure analysis

SUMMARY OF THE INVENTION

A primary object for the invention is to provide a method and apparatus for X-ray angiography that is distinguished by its capability to produce high quality images and image sequences of blood vessels and arterial trees from angiography recordings containing a locally varying motion field due to motion of the patient or motion of the patients inner organs. In addition the method is distinguished by the capability to produce estimates of the contrast flow velocity including estimates of capillary blood flow.

Briefly stated, the invention is based on the use of a shifted adaptive velocity filter. For each local neighbourhood in the signal, the shifted adaptive velocity filter is tuned to compensate for the vessel motion and extract the motion component corresponding to the flow of contrast medium relative to the blood vessels (flow induced motion). By earlier known methods (e.g. subtraction and pixel shift) such a flow induced motion analysis is not possible for an angiography sequence containing a locally varying motion field. The control signal for the shifted adaptive velocity filter is formed either from a set of corresponding points defined externally e.g. by a human operator or automatically by the use of a spatio-temporal filter bank and a priori information about the contrast pulse envelope and statistics of the expected motions. In addition, the method offers the possibility to decrease the amount of contrast fluid injected in the patient without loss in image quality, or using an unaltered amount contrast fluid, obtaining further increased noise suppression and fine detail rendering.

DESCRIPTION OF THE PREFERRED EMBODIMENTS

In general, a spatio-temporal signal such as an angiography sequence is processed with multidimensional signal analysis tools either as a space-time cube where each position (voxel) within the cube are designated e.g. intensity value or in the frequency (Fourier) domain as a function of spatial and temporal frequencies. In this presentation the frequency domain approach will be frequently used. These two aspects of the signal are, however, two sides of the same coin where the relation between the spatial and frequency domain is defined by the Fourier transform [see Bracewell]. The description of the Velocity Adaptive Filtered Angiography-method is simplified if the following expressions and spatio-temporal filtering terms are initially defined.

Background Signals present with or without the presence of contrast fluid.

Contrast induced signals Signals caused by the presence of contrast fluid.

Vessel signals Induced signals due to the motion of blood vessels.

Flow signals Induced signals due to the motion of contrast fluid relative to the blood vessel.

Temporal frequency specific signals Signals having energy contributions mainly in an area of the frequency domain bounded by surfaces given by specified temporal frequencies.

Velocity specific signals Signals having energy contributions mainly in an area of the frequency domain bounded by surfaces given by a specified velocity boundary.

Low velocity signals Signals having energy contributions mainly in areas of the frequency domain bounded by surfaces corresponding to a specified threshold velocity selective magnitude.

Filter Unit that produces an output by combining values in a space-time neighbourhood.

Temporal frequency selective filter Filter which separates temporal frequency specific signals from the remaining part of the signal.

Velocity selective filter Filter which separates velocity specific signals from the remaining part of the signal.

Low velocity filter Filter which separates low velocity signal from the remaining part of the signal.

Figure 5:
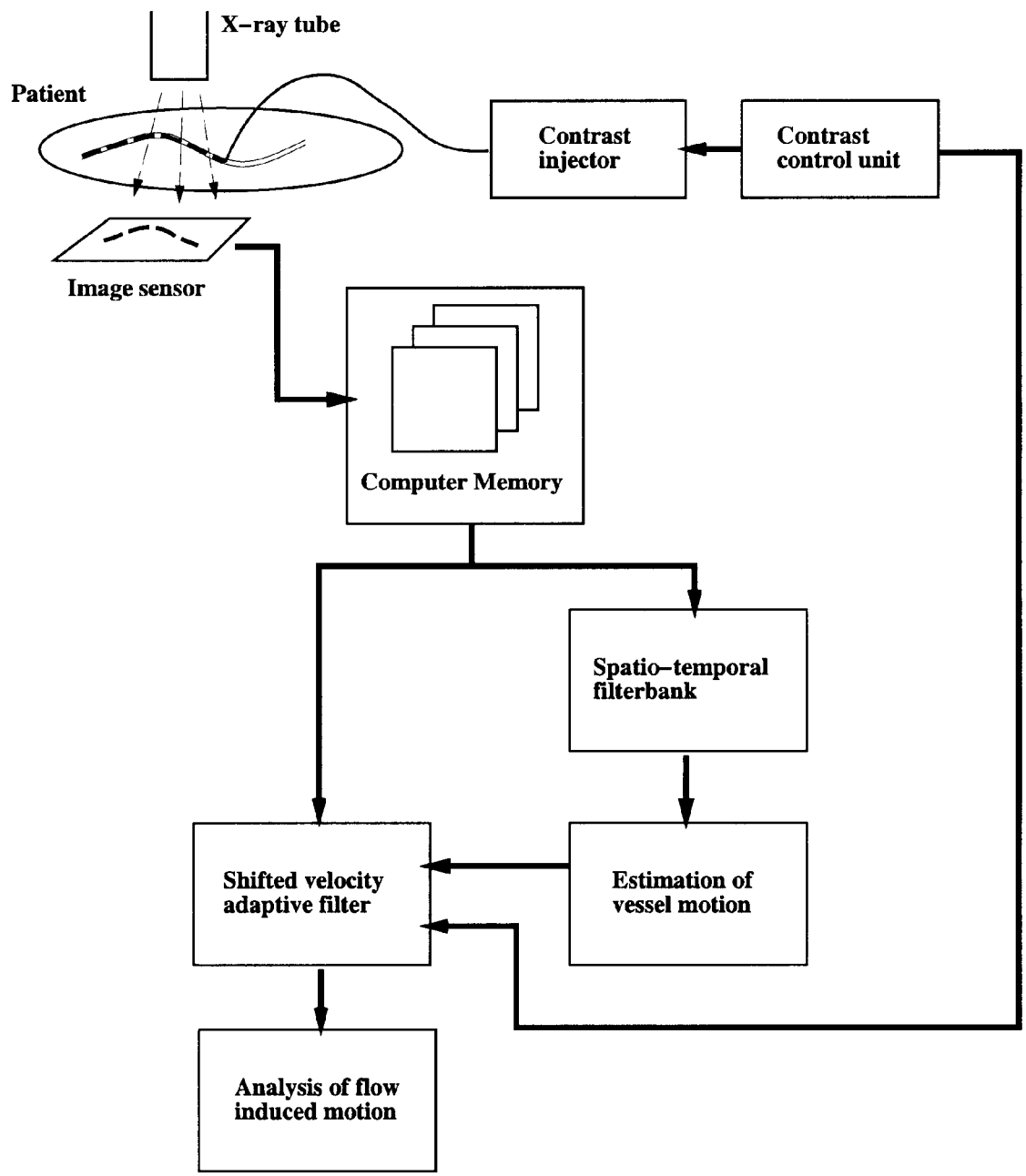
FIG. 5 A block diagram for a system that estimates flow induced motion by the use of a shifted velocity adaptive filter. The system acquires an X-ray angiography image sequence via intra vascular injection of contrast medium. The vessel motion field is estimated by the use of a spatio-temporal filter bank and from the shape of the contrast injection pulse. From this information the shifted velocity adaptive filter extracts the flow induced motion.
Figure 6:
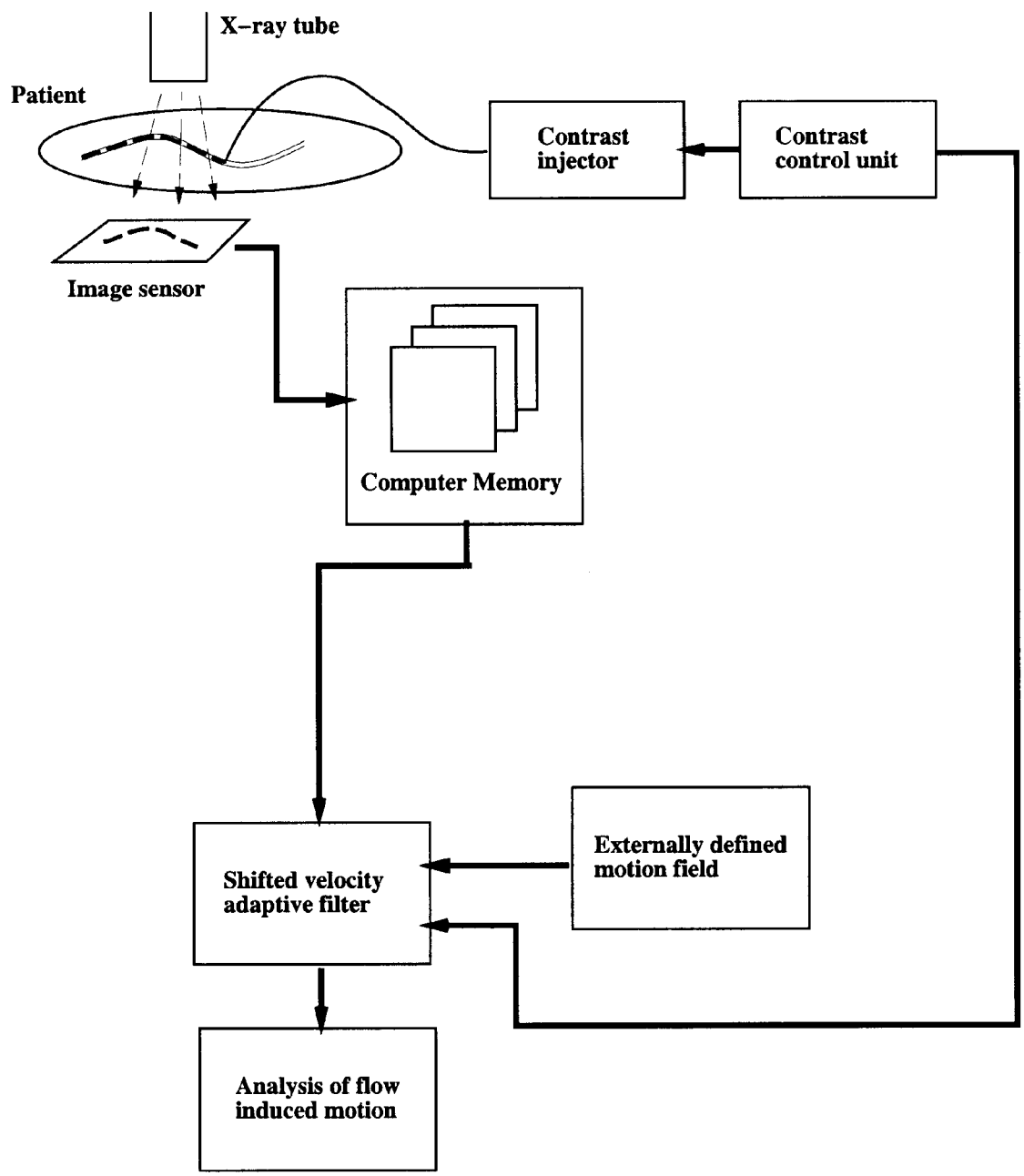
FIG. 6 Relates to FIG. 5 and illustrates an alternative method to compute the locally varying motion field induced by the vessel motion. The motion field is defined externally e.g by a human operator defining a set of characteristic points from which the vessel motion field is computed.
Figure 7:
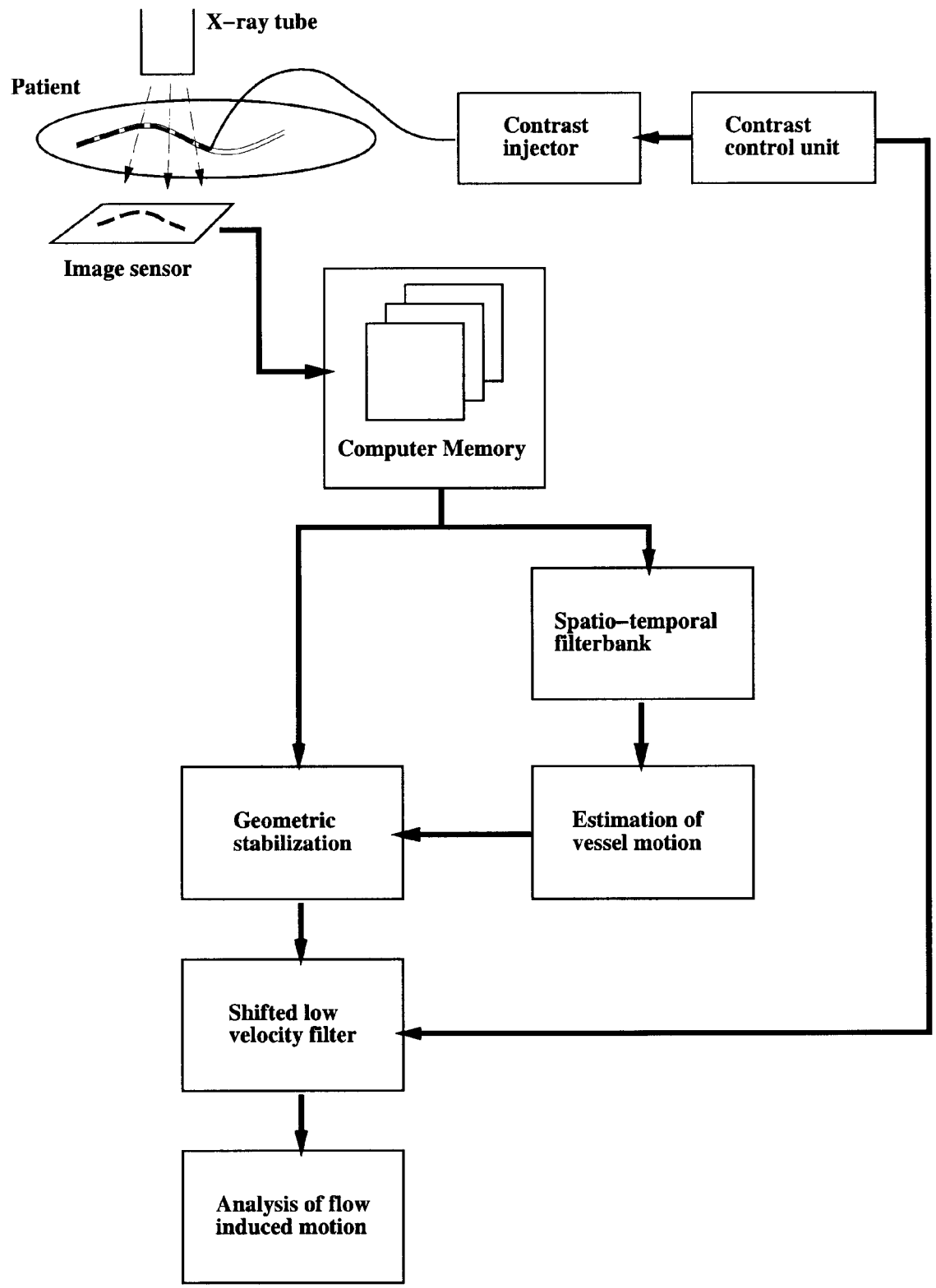
FIG. 7 A block diagram for a system that estimates flow induced motion by the use of geometric remapping and a shifted low velocity filter. The system acquires an X-ray angiography image sequence via intra vascular injection of contrast medium. The vessel motion field is estimated by the use of a spatio-temporal filter bank and from the shape of the contrast injection pulse. From this information the geometric remapping stabilizes the vessels and the shifted low velocity filter extracts the flow induced motion.
Figure 8:
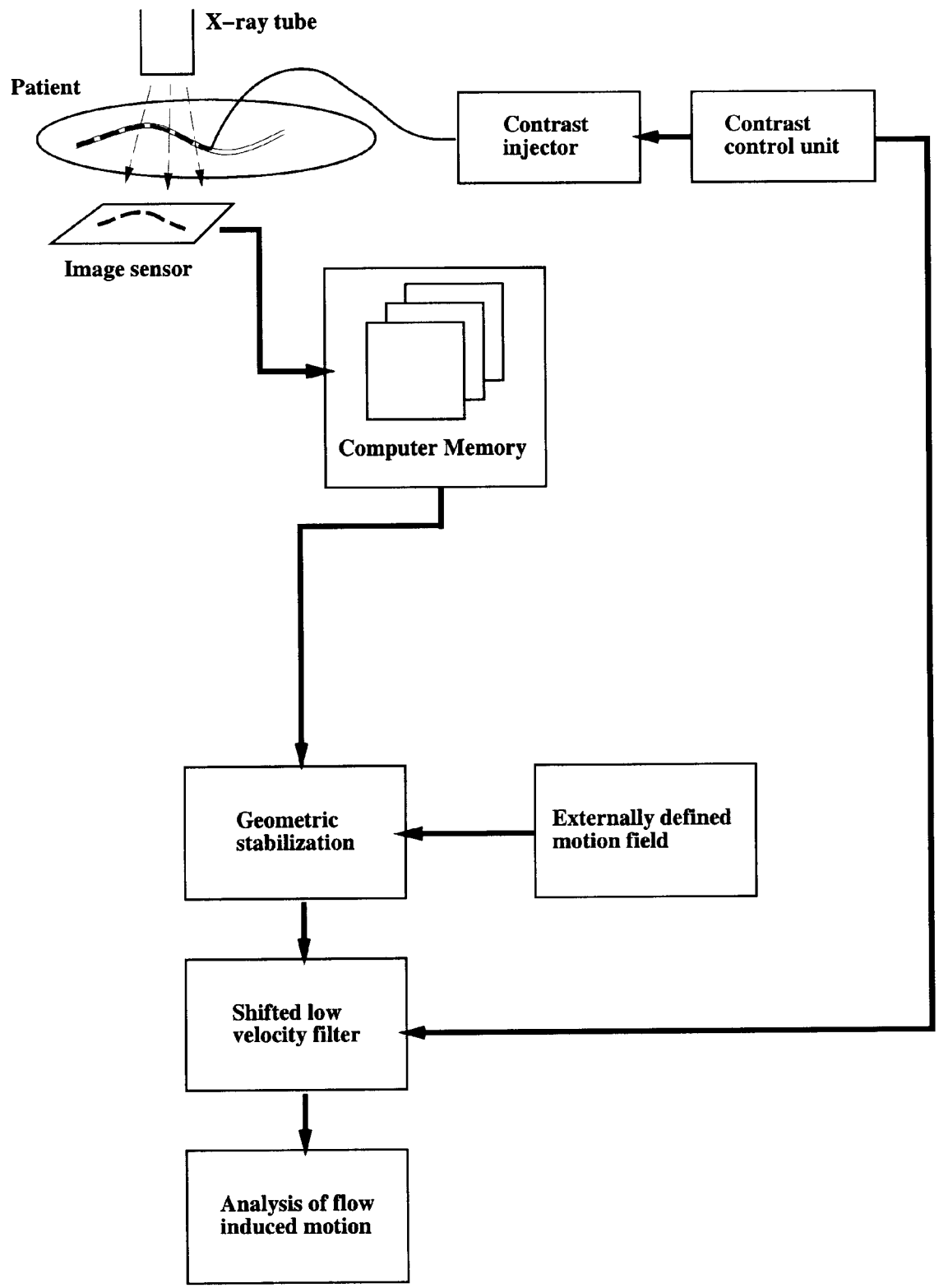
FIG. 8 Relates to FIG. 7 and illustrates an alternative method to compute the locally varying motion field induced by the vessel motion. The motion field is defined externally e.g by a human operator defining a set of characteristic points from which the vessel motion field is computed.

Local velocity estimate A number of local motion estimation methods exists. Here two examples are given. In the first method, which is illustrated in FIG. 6, the motion field is defined externally e.g. by a human operator defining a limited number of corresponding points. By computing the position of each characteristic point as a function of time a sparse motion field is obtained. From this sparse motion field a best matching dense motion field that support the adaptive adaptive filtering can be computed using conventional methods. The second method to compute the motion field is illustrated in FIG. 5 and uses a spatio-temporal filter bank of quadrature filters to automatically extract the motion field according to the principles presented in e.g.[Granlund and Knutsson chapter 6, Fleet].

Shifted velocity selective filter Velocity selective filter which has been shifted along the temporal frequency axis. The shift may be equal to zero yielding a velocity selective filter.

Shifted low velocity filter Low velocity filter that has been shifted along the temporal axis. The shift may be equal to zero to yielding a low velocity filter.

Adaptive filter Unit that produces an output by combining values in each space-time neighbourhood in a way that is dependent on the processed image sequence and separately established for each neighbourhood.

Velocity adaptive filter Adaptive velocity selective filter.

Shifted velocity adaptive filter Adaptive shifted velocity selective filter.

Temporal pulse Deviation from zero only inside a given interval in time.

Consider the upper part in FIG. 5. A patient or the part of the patient that is subject for the angiography examination is placed in between an X-ray tube and an X-ray image intensifier. The X-ray image intensifier converts the projected X-ray image to an electronic signal which is stored in digital form for future processing by computer. To increase the contrast and visibility of the vessels relative to the surrounding tissue a contrast medium is injected. The contrast medium is injected in form of a pulse or as a series of pulses. The shape or frequency content of the contrast injection pulse is essential for the invention and will be discussed later in this section. During the injection phase, the propagation of the contrast medium is recorded and stored as a series of images (image sequence) for further processing. The local motions that occur in such an angiography recording is due to motion of the background or motion of the injected contrast (contrast induced motion). The contrast induced motion can be separated in movements induced by motion of contrast medium relative to the blood vessels (flow signals) and motion of blood vessels carrying contrast (vessel motion). Note that the vessel motion is not a global phenomenon but varies locally with position and time due to the motion of the patient or motion of the patients inner organs e.g. intestine motion, breathing and heart beats.

Figure 1:
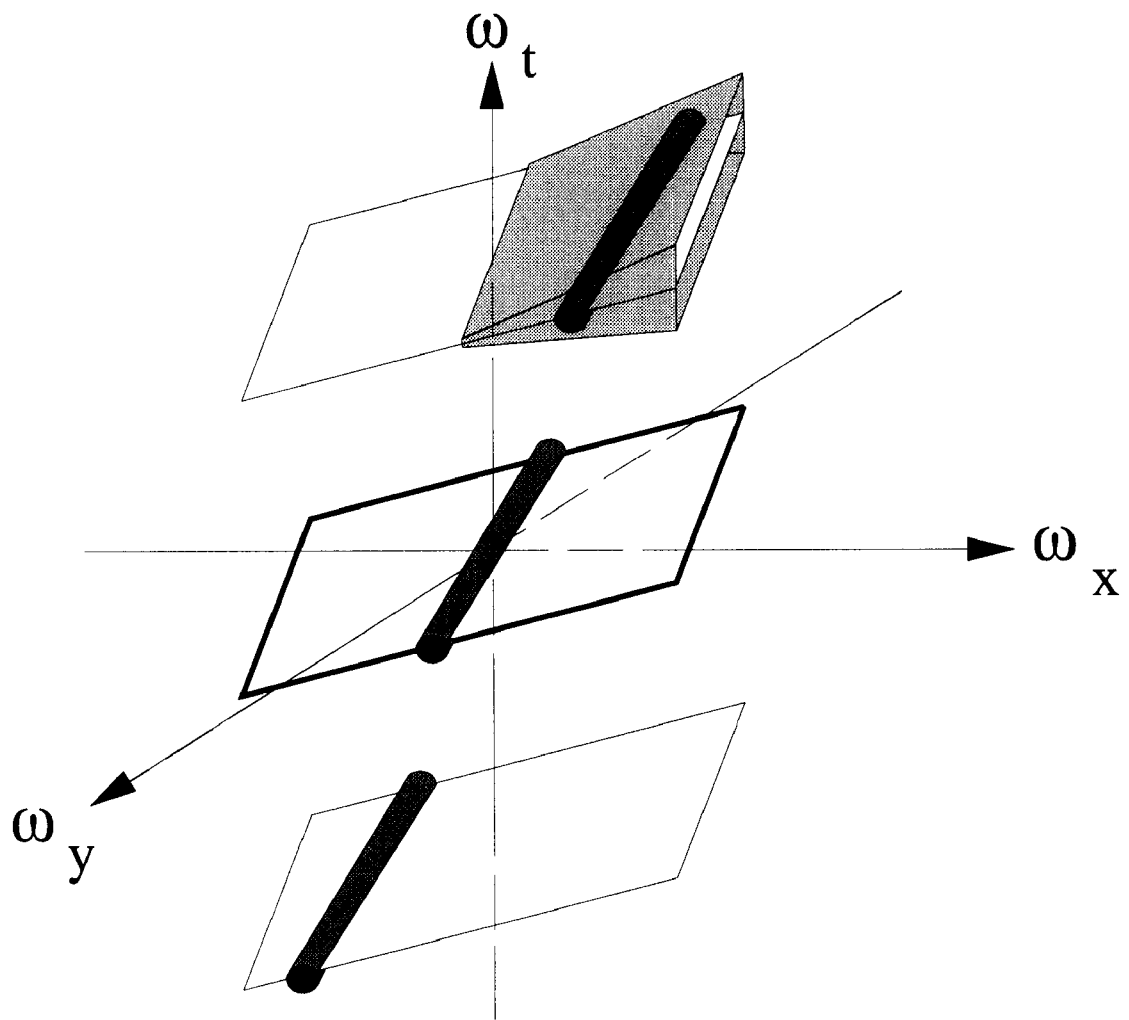
FIG. 1 An illustration of the energy contribution in the Fourier domain for a three dimensional (one temporal and two spatial dimensions) local neighbourhood where both vessel motion and flow induced motion are present The plane indicated by a wide border correspond to the background signals. The inclination of the plane indicate the magnitude and direction of the vessel motion. The energy contributions from the flow induced signals are concentrated on the three cylinders located within the three planes. The positioning of the planes with thin border along the temporal frequency axis is determined by the shape or frequency of the contrast pulse while the position on the plane, indicated by dark cylinders, is dependent on the velocity and direction of the blood flow. An increased flow velocity will move the energy contribution towards the temporal frequency axis while a change in flow direction imply a rotation of the cylinders within the plane. The shaded wedge shaped area indicate the frequency response of a tuned 3-dimensional shifted velocity adaptive filter FIG. 2 In difference to FIG. 1 the inclination of the planes is different which indicate that the vessels moves in a different direction and with increased velocity. The flow induced energy contribution, the dark cylinders, appear in a different orientation within the plane which imply that the blood flow moves in a different direction for this neighbourhood relative to the neighbourhood in FIG. 3.

In FIG. 1 the spectrum of the Fourier transform of a local neighbourhood in an angiography sequence, where the contrast concentration varies in time as a squared cosine, is illustrated. The vertical axis corresponds to the temporal frequency. If no motion is present (no temporal variation) all energy contribution is concentrated to a plane defined by the spatial frequency axes. This observation is used for subtraction angiography which in frequency terms is equivalent to removing the information where the temporal frequency is zero i.e. the background signal. If, however, the patient or the blood vessels are moving the energy will be concentrated along the plane passing through the origin illustrated by a wide border line. The inclination of the plane define both the direction and the magnitude of the motion. The pixel shift operation is in frequency terms described as a rotation which bring the plane back to a position spanned by the spatial axes. Note that the pixel shift operation is global and cannot compensate for locally varying vessel motion.

The injection of the contrast medium in form of a pulse or a series of pulses causes a temporal modulation and the corresponding flow induced energy contribution, indicated by dark cylinders, will be located within three parallel planes according to FIG. 1. The distance between the modulated planes, indicated by thin border lines, and the origin is dependent on the shape or frequency of the contrast pulse. A shorter duration (higher temporal frequency) imply a larger distance (better separation) along the temporal axis. Furthermore the position of the cylinders (the flow induced energy contribution) is dependent on the velocity as well as the direction of the blood flow. A decreased flow velocity will move the energy contribution further out along the planes while the orientation of the cylinders within the planes define the direction of the blood flow.

The flow signals can be separated from the background and vessel signals by processing the X-ray image sequence using a tuned 3-dimensional shifted velocity adaptive filter. The shaded wedge shaped area in FIG. 1 indicate the frequency response of a shifted velocity adapted filter which estimates the flow induced motion without introducing motion artifacts. The shifted velocity adaptive filter is tuned both to the vessel motion i.e. the inclination of the planes and to the position along the temporal axis which correspond to the frequency response of the contrast pulse.

Figure 2:
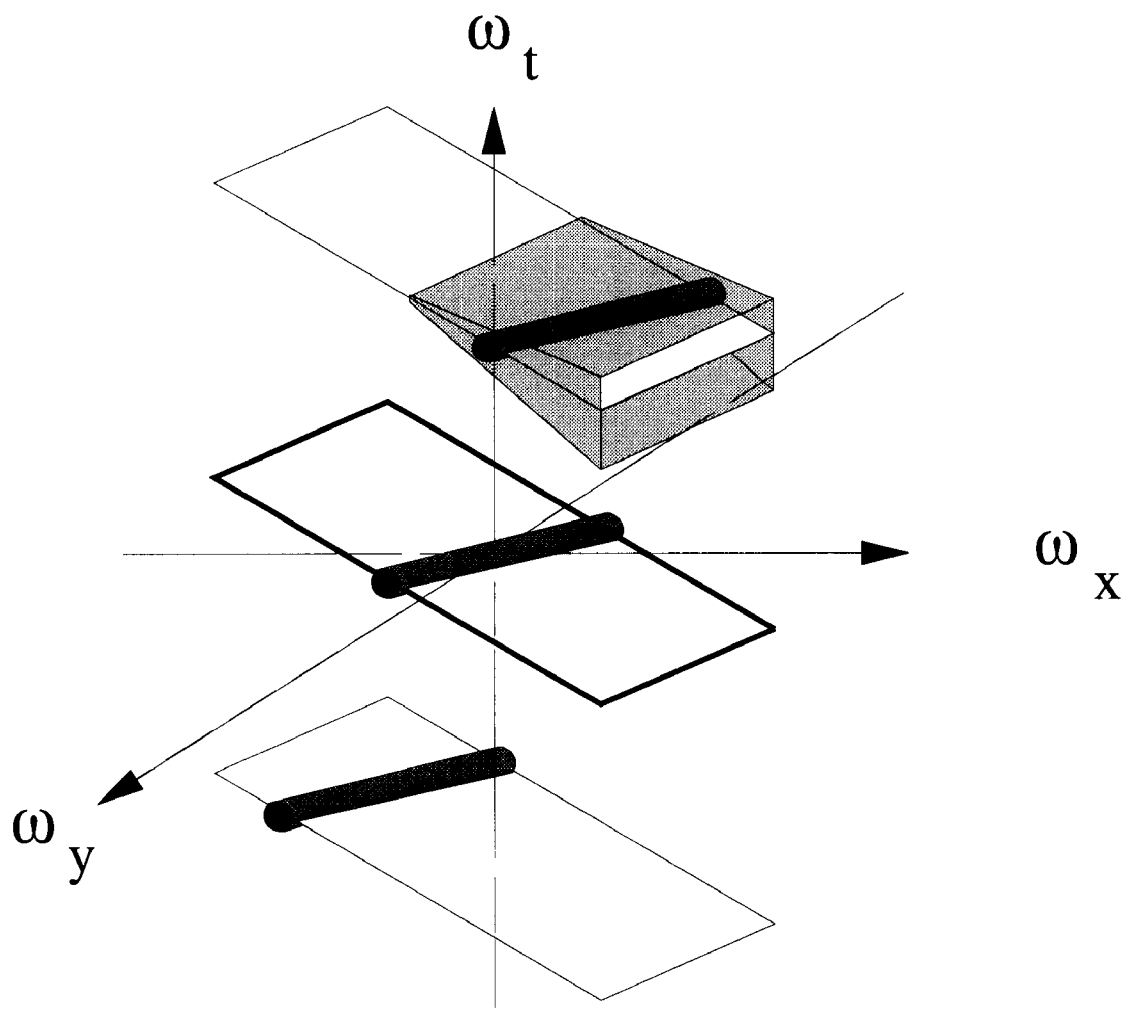

FIG. 2 illustrate an alternative neighbourhood where the vessel motion (the inclination of the planes) and the blood flow (the orientation of the cylinders) occur in different directions relative to FIG. 1. The magnitude of the vessel motion and the flow velocity are approximately equal in FIG. 1 and FIG. 2.

Figure 3:
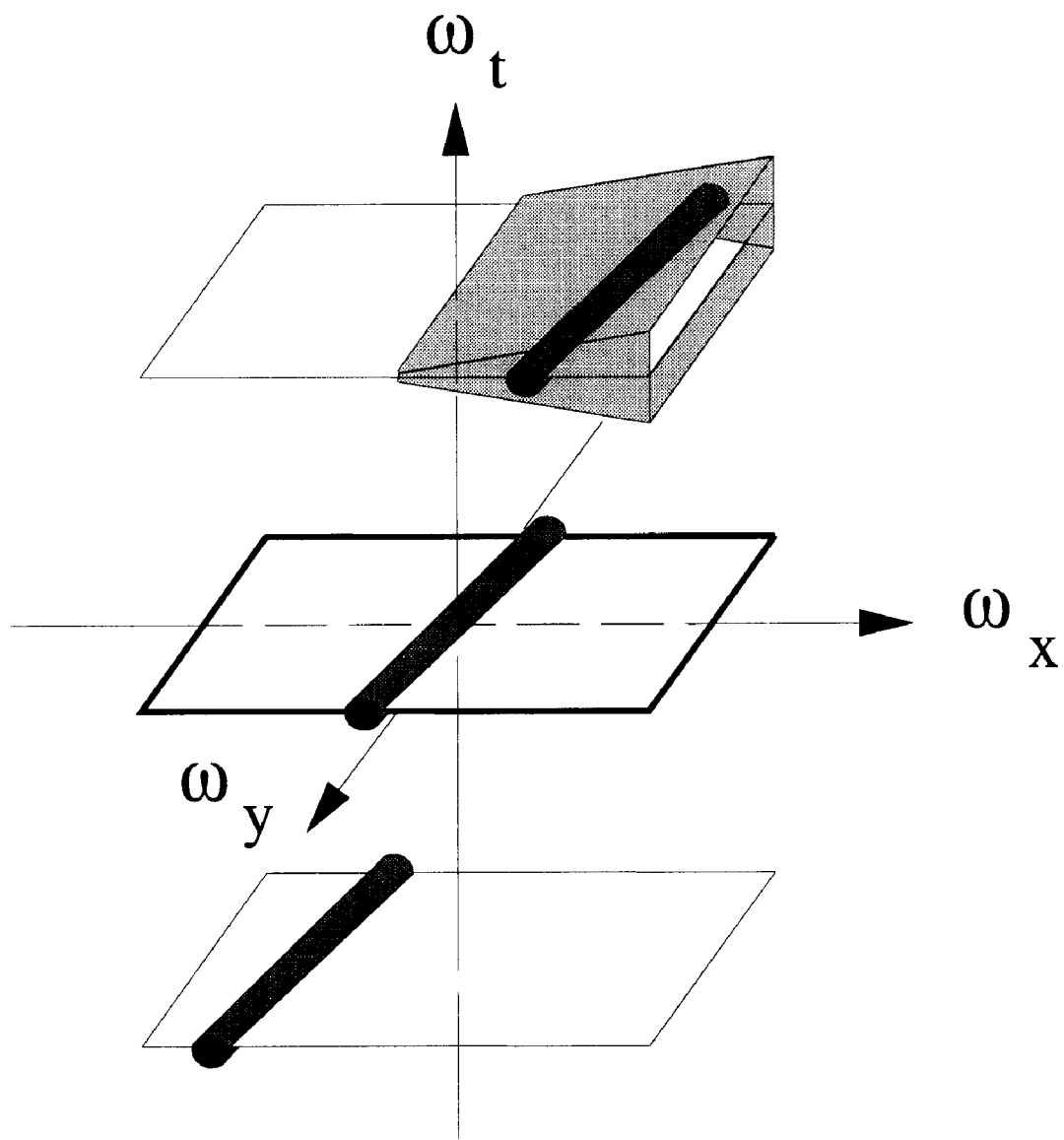
FIG. 3 Illustrates the effect of the velocity adaptive filter on a local neighbourhood where vessel motion is present e.g. the neighbourhoods in FIG. 1 and FIG. 2. The velocity adaptive filter performs the equivalent to a local stabilization of the motion field and at the same time estimates the contrast (blood) flow velocity.

An estimate of the local motion field induced by the vessel motion (the inclination of the planes) is used to specify the center velocity of the velocity adaptive filter. In this way, the velocity adaptive filter performs the equivalent to a local stabilization of the motion field, i.e. the difference between local velocities in the X-ray image sequence and the corresponding center velocities of the shifted velocity adaptive filter will always be small. In FIG. 3 the stabilizing effect of the velocity adaptive filter is illustrated for the neighbourhood in FIG. 1 and FIG. 2.

Figure 4:
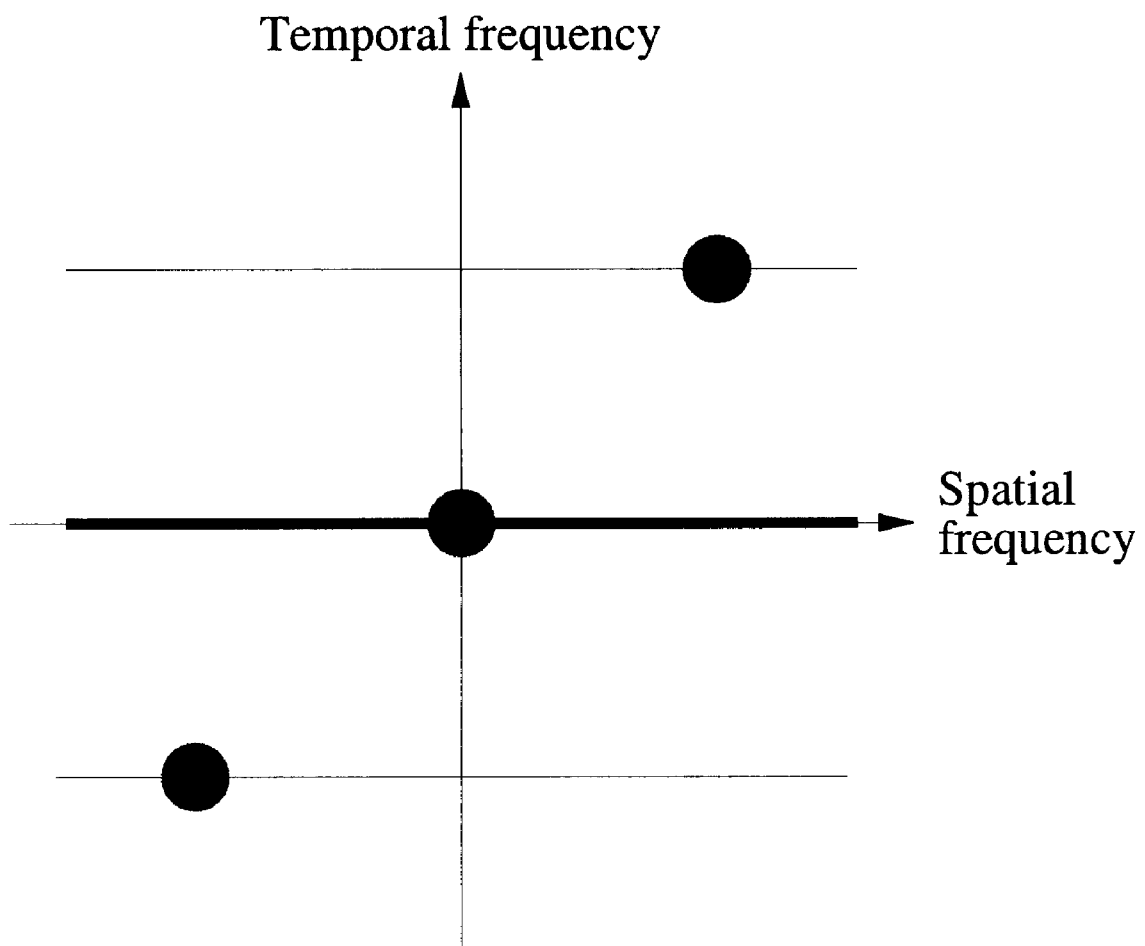
FIG. 4 Illustrates a projection of the local neighbourhood in FIG. 3 in a direction orthogonal to the direction of the blood flow and the temporal axis.

FIG. 4 illustrates a projection of FIG. 3 in a direction orthogonal to the planes defined by the vessel motion and the direction of the blood flow in order to better illustrate the effect of the local stabilization of the vessel motion. From FIG. 4 it is apparent that the background signal and the non-modulated flow induced energy components can be removed by a temporal selective filter which removes low temporal frequency content of the signal enabling an estimation of the flow induced motion by conventional methods. To chose the temporal selective high pass filter it is necessary to have access to the magnitude of the temporal shift (the position of the modulated planes). The local stabilization of the vessel motion comprised by this method supports a robust flow induced motion analysis which is not possible by known methods.

Using a shifted velocity adaptive filter is equivalent to a simultaneous stabilization and flow estimation as described above. Equivalent to the situation described above, the choice of the spatio-temporal filter bank from which the shifted velocity adapted filters are synthesized is based on the magnitude of the temporal shift (the position of the modulated planes) and the estimate of the local motion field induced by the vessel motion (the inclination of the planes) is used to control the shifted velocity adaptive filter.

The magnitude of the shift is dependent on the frequency response of the contrast injection pulse which is obtained from the contrast injector control unit in FIG. 5. In general the separation of the background signal and the flow induced signal is simplified if the magnitude of the temporal shift is increased which imply that short duration (high temporal frequency) contrast pulses simplifies the estimation. The shape of the contrast pulses is however bounded by physical constraints.

Another method of imaging-a blood vessel in a body in accordance with the invention comprise injection of contrast and recording of signals constituted by a series of X-ray images depicting the X-ray attenuation values. Then a geometric remapping of the image sequence is camed out. In this remapping the local coordinates are altered as a function of the movement in the image to bring the image parts that have moved from the preceding image back to the location they had in the previous image. The image is treated as if it was elastic or plastic in the plane and a sub-image depicting a particular part of the pictured body are hereby stabilized over time. This remapping produces a sequence corresponding to slowly moving blood vessels. The essential effect of this procedure corresponds directly to the stabilizing effect performed by the shifted velocity adaptive filter described above, see FIG. 3.

After the geometric stabilizing procedure has been performed the remaining part of the method is identical to the shifted velocity adaptive filter method setting the center velocity to zero everywhere, i.e. using a shifted low velocity filter.

Note that the stabilization obtained using the geometrical remapping is absolute (as opposed to relative in the shifted velocity adaptive filter method) and the resulting sequence will show stationary vessels (however, the background may be moving). Also note that the geometric remapping of the X-ray image sequence may induce minor local geometric distortions and the result of the remapping procedure may to some extent differ also signal separation performance from the shifted velocity adaptive filter method.

An additional benefit of the invented method is that the injection of the contrast medium in form of a pulse or a series of pulses offers the possibility to decrease the amount of contrast fluid injected in the patient while retaining the quality of the produced images or image sequences. The use of a series of pulses in relation to a single pulse concentrate the position of the flow induced energy contribution in the Fourier domain which increases the separation of background and flow induced signals and simplifies the motion estimation. It is consequently possible to control the amount of contrast medium injected relative to the local conditions of the part of the patients body that is subject for examination i.e using a smaller amount of contrast fluid without loss in image quality, or using an unaltered amount contrast fluid, obtaining better noise suppression and enhanced resolution of fine details. In addition the method also presents a means to discriminate and quantify capillary blood flow, e.g. in the heart walls, that has been very difficult to discriminate with previous methods.

For visualizing purposes the method comprises the possibilities to produce relative phase estimates of the contrast flow which e.g. supports the computation of relative arrival time for the contrast flow. The obtained velocity estimates may also be used to produce an image or an image sequence. In addition the method comprises the possibility to render images or image sequences containing synthetically generated contrast pulses for increased visibility of the flow dynamics. For instance a pulse of significantly shorter duration may be synthesized.

References

[1] M. Andersson. *Controllable Multidimensional Filters in Low Level Computer Vision*. PhD thesis, Linköping University, Sweden, S-581 83 Linköping, Sweden, September 1992. Dissertation No 282, ISBN 91-7870-981-4.

[2] R. Bracewell. *The Fourier Transform and its Applications*. McGraw-Hill, 2nd edition, 1986.

[3] D. E. Dudgeon and R. M. Mersereau. *Multidimensional Digital Signal Processing*. Prentice-Hall signal processing series. Prentice-Hall, 1984. ISBN 0-13-604959-1.

[4] D. J. Fleet. *Measurement of image velocity*. Kluwer Academic Publishers, 1992. ISBN 0-7923-9198-5.

[5] G. H. Graulund and H. Knutsson. *Signal Processing for Computer Vision*. Kluwer Academic Publishers, 1995. ISBN 0-7923-9530-1.

[6] H. Knutsson. Representing local structure using tensors. In *The 6th Scandinavian Conference on Image Analysis*, pages 244–251, Oulu, Finland, June 1989. Report LiTH-ISY-I-1019, Computer Vision Laboratory, Linköping University, Sweden, 1989.

[7] H. Knutsson and M. Andersson. Robust N-Dimensional Orientation Estimation using Quadrature Filters and Tensor Whitening. In *Proceedings of IEEE International Conference on Acoustics, Speech, & Signal Processing*, Adelaide, Australia, April 1994. IEEE. LiTH-ISY-R-1798.

We claim:

1. In a method of imaging a blood vessel in a body using X-rays and an injectable contrast medium wherein a contrast medium is injected into the body and signals constituted by an X-ray image sequence depicting X-ray attenuation values is recorded, the improvement which comprises combining X-ray attenuation values in each space-time neighborhood in a way that is dependent on said processed image sequence and separately established for each neighborhood, and separating, from background and vessel signals, flow signals having energy contributions mainly in an area of frequency domain bounded by surfaces corresponding to threshold velocities separately established for each neighborhood, which surfaces are shifted a specified amount along a temporal frequency axis.

2. In a method according to claim 1, the improvement wherein location of flow signals is moved further from the background and from the vessel signals by enforcing a specific temporal variation of the injected amount of contrast medium.

3. In a method according to claim 2, the improvement wherein the contrast medium is injected as a series of temporal pulses.

4. In a method according to claim 2, the improvement wherein the pulse shape is unimodal.

5. In a method according to claim 1, the improvement which comprises the step of estimating local flow velocity as a function of said processed image sequence.

6. In a method according to claim 1, the improvement which comprises the step of estimating local relative phase as a function of said processed image sequence.

7. In a method according to claim 1, the improvement which comprises the step of estimating local relative contrast pulse arrival time as a function of said processed image sequence.

8. In a method according to claim 5, the improvement which comprises producing an image or image sequence as a function of local velocity.

9. In a method according to claim 6, the improvement which comprises producing a resulting image or image sequence as a function of local relative phase.

10. In a method according to claim 7, the improvement which comprises producing an image or image sequence as a function of local relative contrast pulse arrival time.

11. In a method according to claim 1, the improvement which comprises the step of producing a resulting image sequence depicting contrast flow using computer generated virtual contrast pulses.

12. In a method of imaging a blood vessel in a body using X-rays and an injectable contrast medium wherein a contrast medium is injected into the body and signals constituted by an X-ray image sequence depicting X-ray attenuation values is recorded, the improvement which comprises geometric remapping of said image sequence which mapping is dependent on said processed image sequence and separately established for each neighborhood, producing a remapped image sequence corresponding to slowly moving blood vessels, and then removing signals having energy contributions mainly in areas of the frequency domain bounded by surfaces corresponding to a specified threshold velocity magnitude.

13. In a method according to claim 12, the improvement wherein remapping is effected by calculating displacement vectors from externally defined correspondences.

14. In a method according to claim 12, the improvement wherein remapping is effected by calculating displacement vectors from locally estimated velocity in said image sequence.

15. In a method according to claim 14, the improvement wherein a velocity estimation procedure is executed after applying a temporal frequency selective filter tuned to the frequency content of contrast induced signals.

16. In a method according to claim 12, the improvement wherein the amount of contrast medium is injected as a specific temporal variation whereby to move location of the flow signals from background and from vessel signals.

17. In a method according to claim 13, the improvement wherein the amount of contrast medium is injected as a specific temporal variation whereby to move location of the flow signals from background and from vessel signals.

18. In a method according to claim 15, the improvement wherein the amount of contrast medium is injected as a specific temporal variation whereby to move location of the flow signals from background and from vessel signals.

19. In a method according to claim 15, the improvement wherein the contrast medium is injected as a series of temporal pulses.

20. In a method according to claim 19, the improvement wherein the pulse shape is unimodal.

21. In a method according to claim 12, the improvement which comprises the step of estimating local velocity as a function of said processed image sequence.

22. In a method according to claim 12, the improvement which comprises the step of producing local relative phase estimates as a function of said processed image sequence.

23. In a method according to claim 12, the improvement which comprises the step of estimating local relative contrast pulse arrival time as a function of said processed image sequence.

24. In a method according to claim 20, the improvement which comprises the step of producing a resulting image or image sequence as a function of local velocity estimates.

25. In a method according to claim 22, the improvement which comprises producing a resulting image or image sequence as a function of local phase estimates.

26. In a method according to claim 23, the improvement which comprises producing a resulting image or image sequence as a function of local arrival time estimates.

27. In a method according to claim 12, the improvement which comprises producing a resulting image sequence depicting contrast flow using computer generated virtual contrast pulses.

28. In a method of imaging a blood vessel in a body using X-rays and an injectable contrast medium wherein a contrast medium is injected into a body and an X-ray image sequence depicting X-ray attenuation values is recorded, the improvement which comprises combining values in each space-time neighborhood in a way that is dependent on said processed image sequence and separately established for each neighborhood, and separating, from background and vessel signals, flow signals having energy contributions mainly in areas of frequency domain bounded by surfaces corresponding to threshold velocities separately established for each neighborhood, which surfaces are shifted a specified amount along a temporal frequency axis.

29. In a method according to claim 28, the improvement which comprises calculating flow velocity as a function of displacement vectors from externally defined correspondences.

30. In a method according to claim 28, the improvement which comprises calculating velocity regions as a function of displacement vectors from locally estimated velocity in said image sequence.

31. In a method according to claim 30, the improvement wherein velocity is calculated after applying a temporal frequency selective filter tuned to the frequency content of contrast induced signals.

32. In a method according to claim 28, the improvement wherein the amount of contrast medium injected is varied temporarily whereby to move location of flow signals from background and from vessel signals.

33. In a method according to claim 29, the improvement wherein the amount of contrast medium injected is varied temporarily whereby to move location of flow signals from background and from vessel signals.

34. In a method according to claim 31, the improvement wherein the amount of contrast medium injected is varied temporarily whereby to move location of flow signals from background and from vessel signals.

35. In a method according to claim 32, the improvement wherein the contrast medium is injected as a series of temporal pulses.

36. In a method according to claim 31, wherein the pulse shape is unimodal.

37. In a method according to claim 28, the improvement which requires the step of estimating local velocity as a function of said processed image sequence.

38. In a method according to claim 28, the improvement which comprises the step of estimating local relative phase as a function of said processed image sequence.

39. In a method according to claim 28, the improvement which comprises the step of estimating local relative contrast pulse arrival time as a function of said processed image sequence.

40. In a method according to claim 37, the improvement which comprises the step of producing a resulting image or image sequence as a function of velocity estimates.

41. In a method according to claim 38, the improvement which comprises producing a resulting image or image sequence as a function of phase estimates.

42. In a method according to claim 39, the improvement which comprises producing a resulting image or image sequence as a function of arrival time estimates.

43. In a method according to claim 28, the improvement which comprises producing a resulting image sequence depicting contrast flow using computer generated virtual contrast pulses.

* * * * *